United States Patent [19]

Sit et al.

[11] Patent Number: 4,981,991
[45] Date of Patent: Jan. 1, 1991

[54] ANTIHYPERCHOLESTEROLEMIC NITRILE COMPOUNDS

[75] Inventors: Sing-Yuen Sit, Meriden; John J. Wright, Guilford, both of Conn.

[73] Assignee: Bristol-Myers Company, New York, N.Y.

[21] Appl. No.: 484,093

[22] Filed: Feb. 23, 1990

Related U.S. Application Data

[62] Division of Ser. No. 236,563, Aug. 25, 1988, Pat. No. 4,927,944.

[51] Int. Cl.$^5$ .............................................. C07C 255/17
[52] U.S. Cl. ...................................... 558/402; 558/404
[58] Field of Search ................................. 558/402, 404

[56] References Cited

U.S. PATENT DOCUMENTS 3,275,462  9/1966  Strobel et al. .................. 558/402 X
3,280,069  10/1966  Knapp et al. .................... 558/404 X

*Primary Examiner*—Joseph Paul Brust
*Attorney, Agent, or Firm*—Aldo A. Algieri

[57] ABSTRACT

Compounds of the formula

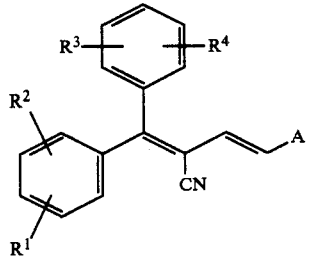

wherein
$R^1$, $R^2$, $R^3$ and $R^4$ each are independently hydrogen, halogen, $C_{1-4}$ alkyl, $C_{1-4}$ alkoxy or trifluoromethyl;
A is

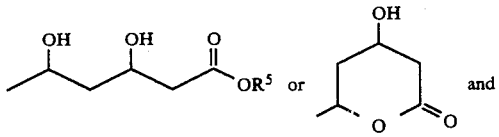

$R^5$ is hydrogen, a hydrolyzable ester group or a cation to a form a non-toxic pharmaceutically acceptable salt, are novel antihypercholesterolemic agents which inhibit cholesterol biosynthesis. Intermediates and processes for their preparation are disclosed.

5 Claims, No Drawings

ANTIHYPERCHOLESTEROLEMIC NITRILE COMPOUNDS

This is a division of our prior co-pending application Ser. No. 236,563, filed Aug. 25, 1988, now U.S. Pat. No. 4,927,944, patented May 22, 1990.

BACKGROUND OF THE INVENTION

1. Field of the Invention

The present invention provides novel tetra substituted olefin compounds which are potent inhibitors of the enzyme 3-hydroxy-3-methylglutaryl coenzyme A (HMG-CoA) reductase and, therefore, are useful in the treatment or prevention of hypercholesterolemia, hyperlipoproteinemia and atherosclerosis. The present invention also provides novel processes for the preparation of the tetra substituted olefin compounds and to certain intermediates in their preparation.

2. Disclosure Statement

The natural fermentation products Compactin (R=H) disclosed by A. Endo, et al. in *Journal of Antibiotics* 29, 1346-1348 (1976) and Mevinolin (R=CH$_3$) disclosed by A. W. Alberts, et al. in *J. Proc. Natl. Acad. Sci. U.S.A.*, 77 3957 (1980) are very active antihypercholesterolemic agents which limit cholesterol biosynthesis by inhibiting the enzyme HMG-CoA reductase, the rate-limiting enzyme and natural point of cholesterogenesis regulation in mammals, including man. Compactin (R=H) and Mevinolin (R=CH$_3$; also known as lovastatin) have the structures shown below:

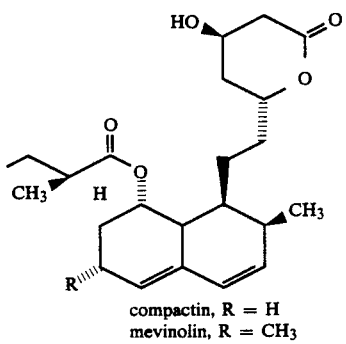

compactin, R = H
mevinolin, R = CH$_3$

A number of structurally related synthetic compounds useful in the treatment of hypercholesterolemia have also been disclosed in patents and other publications. The synthetic art most closely related is as follows:

U.S. Pat. No. 4,198,425, issued Apr. 15, 1980 to S. Mistui, et al. describes novel mevalonolactone derivatives useful for the treatment of hyperlipidemia and having the general formula

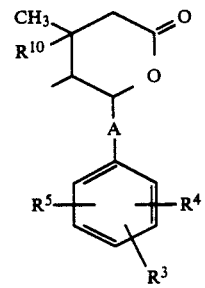

wherein A represents a direct linkage, methylene, ethylene, trimethylene or vinylene group and R$^3$, R$^4$ and R$^5$ represent various substituents.

International patent application No. WO 84/02131 published Jun. 7, 1984 describes analogs of mevalonolactone having the structure

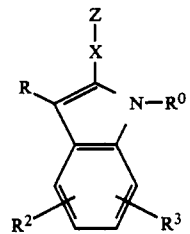

wherein: one of R and R$^0$ is

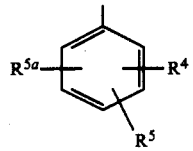

and the other is primary or secondary C$_{1-6}$ alkyl, C$_{3-6}$ cycloalkyl or phenyl—(CH$_2$)$_n$—; X is —(CH$_2$)$_n$—or —CH=CH—; n is 0, 1, 2 or 3; Z is

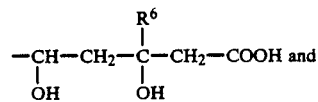

R$^4$, R$^5$, R$^{5a}$ and R$^6$ represent various substituents.

International patent application No. WO 84/02903 published Aug. 2, 1984 describes mevalonolactone analogs having the structures

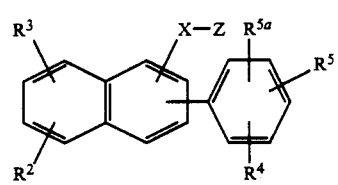

IA

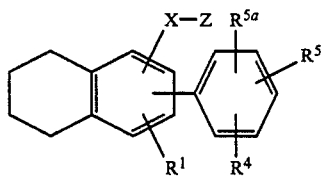

wherein X is —(CH₂)ₙ—,

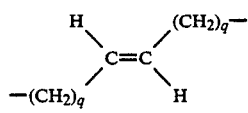

n=0, 1, 2, or 3 and both q's are 0 or one is 0 and the other is 1 and

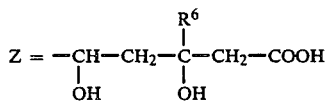

In *J. Med. Chem.*, 28, 347–358 (1985), G. E. Stokker, et al. report the preparation and testing of a series of 5-substituted 3,5-dihydroxypentanoic acids and their derivatives.

In *J. Med. Chem.*, 29, 159–169 (1986), W. F. Hoffman, et al. describe the preparation and testing of a series of 7-(substituted aryl)-3,5-dihydroxy-6-heptenoic (heptanoic) acids and their lactone derivatives. One of the preferred compounds in the reported series has the structure

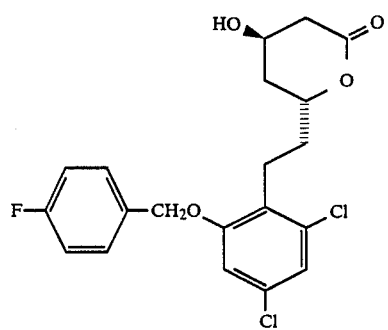

In *J. Med. Chem.*, 29, 170–181 (1986), G. E. Stokker, et al. report the synthesis of a series of 7-[3,5-disubstituted (1,1′-biphenyl)-2-yl]-3,5-dihydroxy6-heptenoic acids and their lactones. Two of the preferred compounds reported in this article have the structures

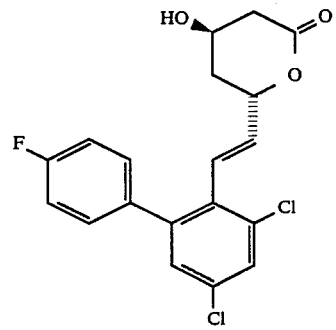

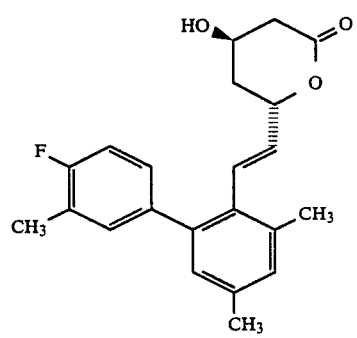

U.S. Pat. No. 4,613,610, issued Sept. 23, 1986 to J. R. Wareing describes pyrazole analogs of mevalonolactone and its derivatives useful for the treatment of hyperlipoproteinemia and atherosclerosis and having the general formula

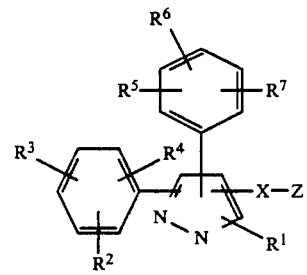

wherein X is —(CH₂)ₙ—, —CH=CH—, —CH=CH—CH₂—or—CH₂—CH=CH—; n is 0, 1, 2 or 3, and R¹, R², R³, R⁴, R⁵, R⁶, R⁷ and Z represent various substituents.

International patent application No. WO 86/07054 published Dec. 4, 1986 describes imidazole analogues of mevalonolactone having the general formula

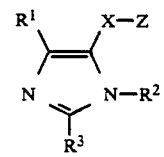

wherein R¹, R² and R³ are C₁₋₆ alkyl not containing an assymmetric carbon atom, C₃₋₇ cycloalkyl, adamantyl-1 and R³ may also be styryl or R¹, R² and R³ are

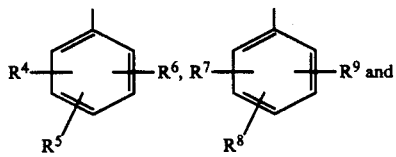

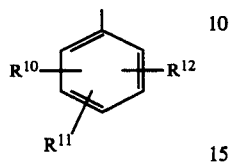

respectively, wherein $R^4$ to $R^{12}$ are various substituents; X is $-(CH_2)_m-$, $-CH=CH-$, $-CH=CH-CH_2$ or $-CH_2-CH=CH_2-$ wherein m is 0, 1, 2 or 3 and Z is

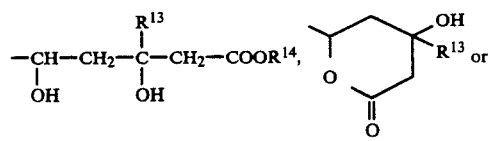

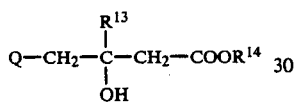

U.S. Pat. No. 4,681,893 issued Jul. 21, 1987 to B. D. Roth describes certain pyrrol-1-yl compounds which are useful as hypocholesterolemic and hypolipidemic agents having the general formula

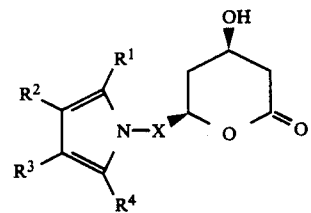

wherein X is $-CH_2-$, $-CH_2CH_2-$, $-CH_2CH_2CH_2-$, or $CH_2CH(CH_3)-$; and $R^1$, $R^2$, $R^3$ and $R^4$ represent various substituents.

U.S. Pat. No. 4,735,958 issued Apr. 5, 1988 to B. D. Roth et al describes certain pyrrol-1-yl compounds which are useful as hypocholesterolemic and hypolipidemic agents having the general formula

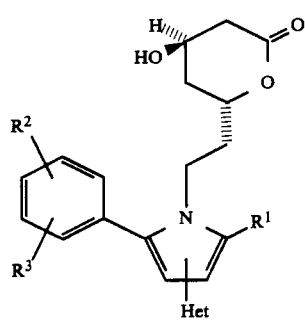

wherein $R^1$, $R^2$, $R^3$ and Het represent various substituents.

SUMMARY OF THE INVENTION

This invention provides novel compounds having the formula

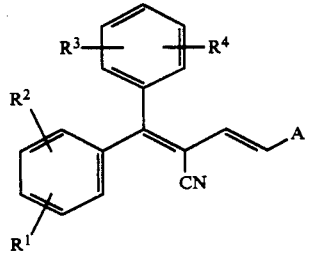

I wherein $R^1$, $R^2$, $R^3$, and $R^4$ are as defined below, which are potent inhibitors of the enzyme 3-hydroxy-3-methylglutaryl coenzyme A (HMG-CoA) reductase and are useful in the treatment of hypercholesterolemia, hyperlipoproteinemia and atherosclerosis. The present invention also provides useful intermediates, processes for their preparation and processes for the preparation of compounds of the Formula I.

DESCRIPTION OF THE INVENTION

The present invention provides novel tetra substituted olefin compounds which are inhibitors of the enzyme HMG-CoA reductase, which are useful in the treatment of hypercholesterolemia hyperlipoproteinemia and atherosclerosis and which have the formula

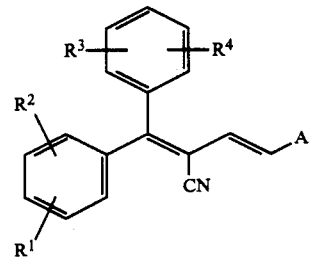

I wherein
$R^1$, $R^2$,
$R^3$ and $R^4$ each are independently hydrogen, halogen, $C_{1-4}$ alkyl, $C_{1-4}$ alkoxy or trifluoromethyl;
A is

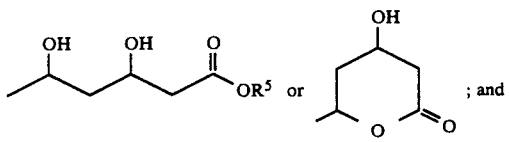

; and $R^5$ is hydrogen, a hydrolyzable ester group or a cation to form a non-toxic pharmaceutically acceptable salt.

This invention also provides processes for the preparation of the compounds of Formula I and to intermediates in the preparation of compounds of Formula I.

The terms "$C_{1-4}$ alkyl", "$C_{1-6}$ alkyl" and "$C_{1-4}$ alkoxy" as used herein and in the claims (unless the context indicates otherwise) means unbranched or branched chain alkyl or alkoxy groups such as methyl, ethyl, propyl, isopropyl, butyl, isobutyl, t-butyl, amyl, hexyl, etc. Preferably, these, groups contain from 1 to 4 carbon atoms and, most preferably, they contain 1 or 2 carbon atoms. Unless otherwise specified in the particular instance, the term "halogen" as used herein and in the claims is intended to include chlorine, fluorine, bromine and iodine while the term "halide" as used herein and in the claims is intended to include chloride, bromide and iodide anion. The term "a cation to form a non-toxic pharmaceutically acceptable salt" as used herein and in the claims is intended to include nontoxic alkali metal salts such as sodium, potassium, calcium and magnesium, the ammonium salt and salts with non-toxic amines such as trialkylamines, dibenzylamine, pyridine, N-methylmorpholine, N-methylpiperidine and other amines which have been used to form salts of carboxylic acids. Unless otherwise specified, the term "a hydrolyzable ester group" as used herein and in the claims is intended to include an ester group which is physiologically acceptable and hydrolyzable under physiological conditions such as $C_{1-6}$ alkyl, phenylmethyl and pivaloyloxymethyl.

In the compounds of Formula I, it is intended that all of the double bonds are in the trans configuration, i.e., (E), as indicated in the structural formulae used herein and in the claims.

As the compounds of the present invention may possess one or two asymmetric carbon atoms, the invention includes all of the possible enantiomeric and diastereomeric forms of the compounds of Formula I as described herein and in the claims. The compounds of Formula I which contain two centers of asymmetry may produce four possible stereoisomers designated as the RR, RS, SR and SS enantiomers; all four stereoisomers are considered within the scope of this invention. Specifically, the compounds of Formula I having two asymmetric carbon atoms bearing the hydroxy groups in the 3 and 5 position may produce four possible stereoisomers which are designated as the (3R,5S), (3S,5R), (3R,5R) and (3S,5S) stereoisomers. As used herein and in the claims, the term "(±)-erythro" is intended to include a mixture of (3R,5S) and (3S,5R) enantiomers, and the term "(±)-threo" is intended to include a mixture of (3R,5R) and (3S,5S) enantiomers. The use of a single designation such as (3R,5S) is intended to include mostly one stereoisomer. The lactone forms of the compounds of Formula I also have two asymmetric carbon atoms at the 4 and 6 position, and the resulting four stereoisomers may be designated as the (4R,6S), (4S,6R), (4R,6R) and (4S,6S) stereoisomers. As used herein and in the claims, the term "trans" lactone is intended to include a mixture of (4R,6S) and (4S,6R) enantiomers while the term "cis" lactone is intended to include a mixture of (4R,6R) and (4S,6S) enantiomers. Mixtures of isomers can be separated into individual isomers according to methods which are known per se, e.g. fractional crystallization, adsorption chromatography or other suitable separation processes. Resulting racemates can be separated into antipodes in the usual manner after introduction of suitable salt-forming groupings, e.g. by forming a mixture of diastereoisomeric salts with optically active salt-forming agents, separating the mixture into diastereomeric salts and converting the separated salts into the free compounds. The possible enantiomeric forms may also be separated by fractionation through chiral high pressure liquid chromatography columns.

If it is desired to prepare the (+) isomer of the compounds of Formula I, then the synthetic (±) isomer of the present invention may be resolved by resolution methods well-known to those skilled in the art. For example of a resolution procedure in this general class of compounds, U.S. Pat. No. 4,375,475 issued Mar. 1, 1983 to A. K. Willard, et al. describe the resolution of a racemic (±) trans lactone with excess d-(+)-α-methylbenzylamine (or the corresponding 1-(−)-α-methylbenzylamine), separating the resulting two diastereoisomeric amines and hydrolyizng to the corresponding, for example, sodium salt. The resulting salt may then be converted by conventional means to the corresponding acid, ester and lactone. Preferably, the optically active enantiomers of the compounds of Formula I may be prepared by stereoselective synthetic procedures, some of which are described herein. The use of optically active reagents in combination with the appropriate intermediate described herein would produce the desired enantiomer of the compound of Formula I.

Since the compounds of Formula I may contain varying amounts of solvent as ascertained mainly by elemental analysis, the present invention is intended to include solvates of the compounds of Formula I. In some cases, it appears that the products may be true solvates, while in other cases, the products may merely retain adventitious solvent or be a mixture of solvate plus some adventitious solvent. Preferably, the solvate is water and, most preferably, one to three moles of water. The examples below give the amount of solvent where appropriate in the analysis and melting points are those of the solvated product unless otherwise indicated.

In the compounds of Formula I, $R^1$, $R^2$, $R^3$, and $R^4$, independently, are preferably hydrogen, fluoro, chloro, methyl or methoxy, and most preferably, $R^1$ and $R^3$ are hydrogen and $R^2$ and $R^4$, independently, are hydrogen, fluoro, methyl or methoxy. Preferably, $R^5$ is hydrogen, $C_{1-6}$ alkyl or a pharmaceutically acceptable cation. Most preferably, $R^5$ is a pharmaceutically acceptable cation especially sodium or potassium.

In the compounds of Formula I wherein A contains two asymmetric carbon atoms bearing the hydroxy group, the erythro isomer is preferred and the (3R,5S) isomer being most preferred. In the compounds of Formula I wherein A contains two asymmetric carbon atoms in the lactone form, the trans isomer is preferred and the (4R,6S) isomer being most preferred.

The compounds of Formula I may be prepared by various procedures, preferably starting from a compound of Formula II

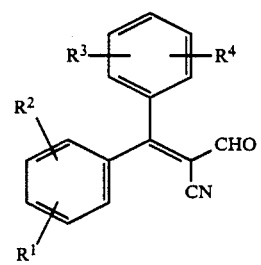

II wherein $R^1$, $R^2$, $R^3$ and $R^4$ each are independently hydrogen, halogen, $C_{1-4}$ alky, $C_{1-4}$ alkoxy or trifluoromethyl.

The compounds of Formula II may be prepared from the optionally substituted benzophenones III by aldol condensation to the tetra substituted olefin V then hydrolyzed and converted to the acyl chloride VI followed by reduction of the acyl chloride in compound VI with subsequent oxidation of the resulting alcohol VII, as shown in Reaction Scheme 1.

Reaction Scheme 1

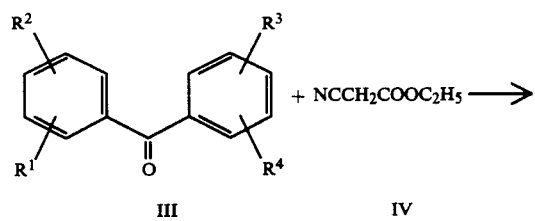

III          IV

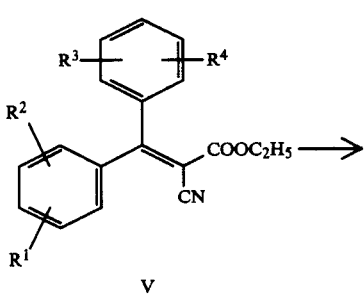

V

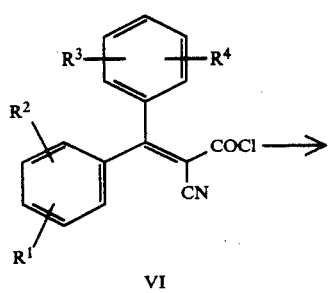

VI

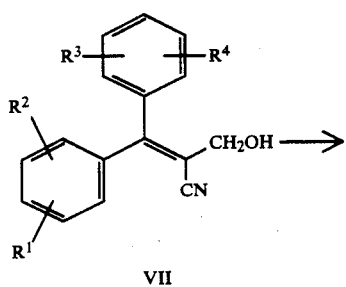

VII

-continued
Reaction Scheme 1

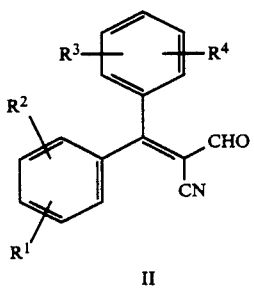

II

In Reaction Scheme 1, $R^1$, $R^2$, $R^3$ and $R^4$ are as previously defined. The optionally substituted benzophenones of the Formula III may be prepared by the general and well-known Friedel Crafts reaction of a substituted phenyl catalyzed by Lewis acids, e.g., with aluminum chloride in carbon tetrachloride at about 0° C. A large number of substituted benzophenones are known and their preparation are described in the art while many others are commercially available. For example, many of the starting materials of Formula III are described by G. Olah in *Friedel-Crafts and Related Reactions, Vol.* 3, Part 1 and 2, Interscience Publishers, New York, 1964 and references therein. The Friedel Crafts reaction may produce a mixture of benzophenones and, if so produced, the mixture may be separated by conventional techniques known in the art.

The appropriate benzophenone of the Formula III may be treated with ethyl cyanoacetate in a solvent mixture containing glacial acetic acid and an organic solvent such as benzene or toluene in the presence of a catalyst preferably β-alanine. The reaction is allowed to proceed at the reflux temperature of the solvent and the water which is produced is azeotropically removed with a Dean-Stark trap or similar apparatus until the production of the tetra substituted olefin V is essentially complete The nitrile ester of the Formula V may then be converted by standard techniques to the alcohol VII by a series of known reactions. According to one reaction route, the compound of Formula V is first hydrolyzed by conventional methods, such as base hydrolysis, i.e., lithium hydroxide, potassium hydroxide and sodium hydroxide. The resulting acid is then converted to an acyl chloride by reacting with a reagent such as oxalyl chloride in methylene chloride at reflux temperature and the resulting acyl chloride of Formula VI is then reduced with a reducing agent, preferably, lithium aluminum hydride in tetrahydrofuran at −78° C. to produce an alcohol of the Formula VII.

The allylic alcohol of Formula VII may be readily oxidized by conventional oxidizing agents such as pyridinium chlorochromate in a non-reactive solvent, preferably, methylene chloride at ambient temperature to produce the corresponding allylic aldehydes of Formula II.

The compounds of Formula I may be prepared from a novel aldehyde of the Formula II wherein $R^6$ is a hydrolyzable ester group and $R^1$, $R^2$, $R^3$ and $R^4$ are as previously defined by the general reaction route shown in Reaction Scheme 2.

Reaction Scheme 2

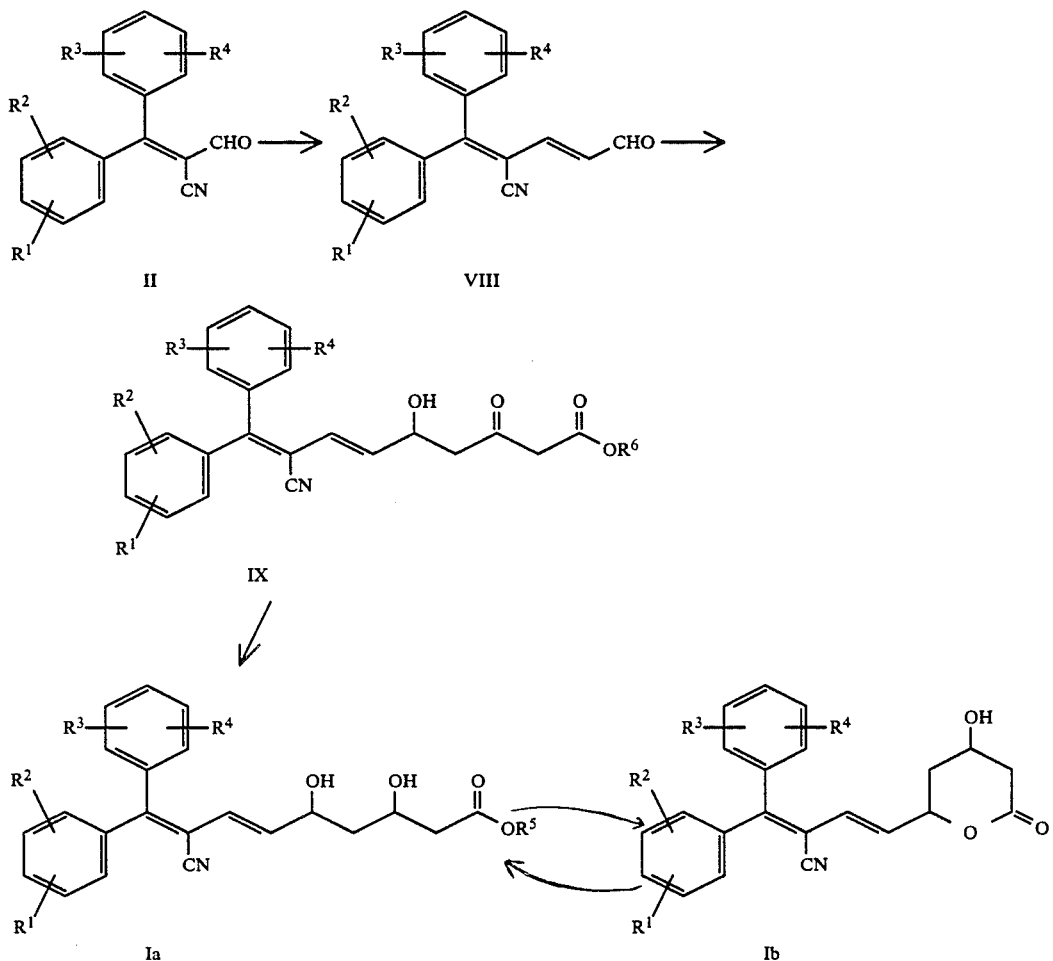

In Reaction Scheme 2, an allylic aldehyde of Formula II may be treated with triphenylphosphoranylidene acetaldehyde in a non-reactive solvent such as benzene, toluene, tetrahydrofuran, 1,2-dimethoxyethane and the like to produce an aldehyde of Formula VIII. The temperature of the reaction is not critical and can be conducted at from ambient temperature to the reflux temperature of the solvent. For convenience we prefer to conduct the reaction at reflux temperature. It should be understood and appreciated by those skilled in the art that the reaction conditions and the number of equivalents of triphenylphosphoranylidene acetaldehyde utilized per equivalent of a compound of Formula II is critical. Preferably, the reaction is conducted with about one equivalent of Wittig reagent under controlled reaction conditions.

The penultimate intermediate of Formula IX wherein $R^6$ is a hydrolyzable ester group such as methyl, ethyl and t-butyl ester may be prepared from the corresponding aldehyde of Formula VIII by reaction with the dianion of acetoacetate ester generated in situ, for example, as described in Example 5. The reaction may be conducted in an inert organic solvent such as tetrahydrofuran at low temperatures from −78° C. to about 0° C. and preferably from about −78° C. to −40° C. until the reaction is essentially complete. The ketone ester of Formula IX may be reduced to the dihydroxy ester of Formula Ia by reduction of the ketone radical with reducing agents well-known in the art, e.g., sodium borohydride, sodium cyanoborohydride, zinc borohydride, disiamylborane, diborane, ammonia borane, t-butylamine borane, pyridine borane, lithium tri-s-butyl-borohydride or other similar reducing agents which will not reduce nor hydrolyze the carboxylic ester radical. Preferably, the reduction is carried out in a stereospecific manner by a two-step stereospecific reduction in order to maximize the production of the preferred erythro isomer of the compound of Formula I. The stereospecific reduction of a compound of Formula IX is carried out with trisubstituted alkylboranes, preferably triethylborane, or alkoxydialkylborares, preferably methoxydiethylborane or ethoxydiethylborane [Tetrahedron Letters, 28, 155 (1987)] at a temperature of about −70° C. to about ambient temperature. The complex which is produced is then reduced with sodium borohydride at a temperature of about −50° C. to about −78° C. in an inert organic solvent such as tetrahydrofuran, diethyl ether and 1,2-dimethoxyethane, preferably, tetrahydrofuran. The reduction is then completed by the addition of methanol. The resulting compound of Formula Ia produced from the stereospecific reduction contains two asymmetric carbon atoms bearing the hydroxy group in an erythro configuration. Thus, reduction of the ketone radical under the conditions employed herein produces mostly the erythro isomers of the compounds of Formula Ia and only a small amount of the less preferred threo isomers. The ratio of erythro-threo isomers produced will vary according to the specific compound utilized and the reaction conditions employed. Normally, this ratio will be approximately 9:1 to 9.8:0.2. However, the use of a non-specific reduction will normally produce a 1:1 mixture of isomers. Nevertheless, the mixture of isomers may be separated and purified by conventional techniques and then converted to the compounds of general Formula I in a conventional manner well-known to those skilled in the art.

The preparation of a compound of Formula Ia wherein $R^5$ is a cation is preferably carried out by base hydrolysis of a compound of Formula Ia wherein $R^5$ is a hydrolyzalable ester group with bases such as sodium hydroxide, potassium hydroxide and lithium hydroxide in an organic solvent such as tetrahydrofuran, ethanol and methanol at a temperature from 0° C. to about 50° C. The form of the cation is normally determined by the corresponding cation of the hydroxide employed. However, if desired, the cation may be exchanged for another cation by treatment with ion-exchange resins.

The compound of Formula Ia may be cyclized to the corresponding lactone of Formula Ib by conventional lactonization methods, for example, by heating the acid in an inert organic solvent such as benzene, toluene and xylene and azetropically removing the water which is produced or by treating the compound of Formula Ia in an inert organic solvent, e.g., toluene, benzene, diethyl ether or methylene chloride with an acid such as p-toluenesulfonic acid in the presence of a drying agent, e.g., NaSO$_4$, MgSO$_4$ or molecular sieves. Preferably, the lactonization may be carried out by activation of the carboxyl radical with a carbodiimide in an inert organic solvent such as tetrahydrofuran, and preferably, in methylene chloride or ethyl acetate at about ambient temperature to produce the lactone of Formula Ib. If the relative stereochemical configuration of the two carbon atoms bearing the hydroxy groups are established as erythro in Formula Ia, then the lactonization will produce the preferred trans lactone of Formula Ib, otherwise the lactonization will produce a mixture of trans and cis lactones. The resulting lactone of Formula Ib may, if desired, be hydrolyzed with base or acid to produce the compounds of Formula Ia.

In an alternate reaction route, the preparation of compounds of Formula I may be prepared from intermediates of Formula XI, as shown in Reaction Scheme 3.

Reaction Scheme 3

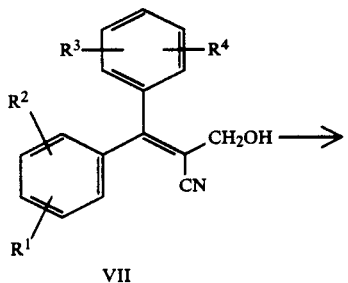

VII

-continued
Reaction Scheme 3

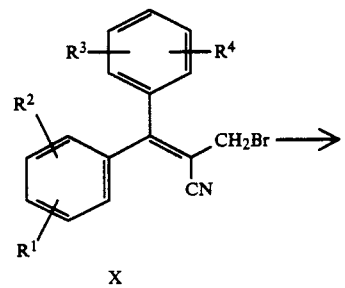

X

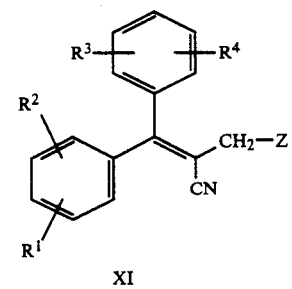

XI

In Reaction Scheme 3, $R^1$, $R^2$, $R^3$ and $R^4$ are as previously defined and Z is

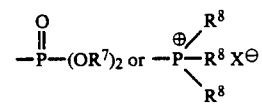

in which $R^7$ is $C_{1-4}$ alkyl, $R^8$ is phenyl which is unsubstituted or substituted by one or two $C_{1-4}$ alkyl or chloro substituents and X is bromo, chloro or iodo. The allylic bromide of Formula X may be prepared from the alcohol of Formula VII by treatment with carbon tetrabromide and triphenylphosphine.

The allylic bromide of Formula X may be reacted in a conventional manner with phosphines such as triphenylphosphine in an inert organic solvent such as cyclohexane to produce the phosphonium salt of Formula XI. Alternatively, the allylic bromide of Formula X may be reacted in a conventional manner with phosphites such as trimethyl phosphite and triethyl phosphite either neat or in an inert organic solvent, and preferably, neat to produce the phosphonates of Formula XI.

The compounds of Formula I may be prepared from an intermediate of Formula XI by the reaction with aldehyde intermediates well known to those skilled in the art. The phosphonium salt or phosphonate of Formula XI may be reacted with silyl protected aldehydes in a similar manner as described in Tetrahedron Letters, 25, 2435 (1984) and U.S. Pat. No. 4,571,428 to produce erythro compounds of Formula Ia. A compound of Formula XI may also be reacted with optically active aldehydes as described in *Tetrahedron Letters*, 23, 4305 (1982) and U.S. Pat. No. 4,613,610 to produce the (4R,6S) enantiomer of a compound of Formula Ib which can, if desired, be converted to the (3R, 5S) enantiomer of a compound of Formula Ia. The methods described above as well as other methods are described in U.S. Pat. Application Ser. No. 151,513 filed Feb. 18, 1988 by us, now U.S. Pat. No. 4,897,490.

When it is desired to prepare mostly one stereoisomer of a compound of Formula I, it is preferred to employ optically pure starting materials. The various procedures which may be used to prepare one isomer of a compound of Formula I is illustrated in Reaction Schemes 4 and 5. The most preferred isomer of a compound of Formula I wherein A is defined as

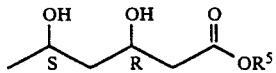

is the (3R, 5S) isomer, and the most preferred isomer of a compound of Formula I wherein A is defined as

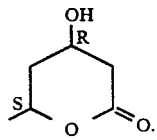

is the (4R,6S) isomer. It should be appreciated that it is necessary to have only one of the above definitions of A for compounds of Formula I since they may be interconverted as shown in Reaction Scheme 2. To illustrate the use of optically pure starting materials, the preparation of a preferred embodiment of compounds of Formula I such as the (3R,5S) isomer of compounds of Formula Ia and the (4R, 6S) isomer of compounds of Formula Ib is shown in Reaction Scheme 5.

Another particularly preferred method envisioned for the preparation of compounds of the Formula Ia and Ib of the present invention is the use of intermediates having the formulae

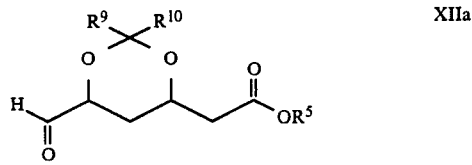

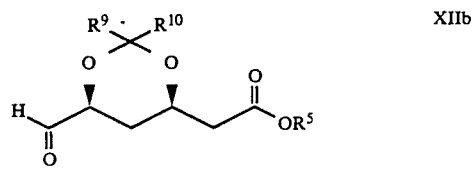

in substantially the cis form wherein $R^9$ and $R^{10}$ each are $C_{1-4}$ alkyl or $R^9$ and $R^{10}$, taken together with the carbon atom to which they are attached, is cyclopentyl, cyclohexyl or cycloheptyl and is hydrogen, $C_{1-4}$ alkyl or a metal cation. The preparation and use of the compounds of Formulae XIIa and XIIb is described herein and in U.S. Pat. Application Ser. No. 156,865, filed Feb. 18, 1988 by William T. Han and John J. Wright, now U.S. Pat. No. 4,824,959 intermediates of Formula XIIa and Formula XIIb is shown in Reaction Schemes 4 and 5, respectively.

Reaction Scheme 4

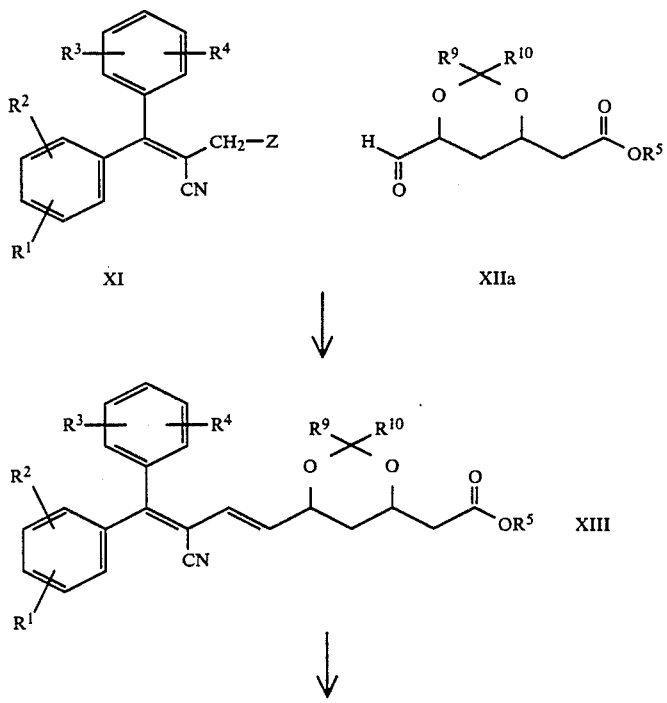

-continued
Reaction Scheme 4
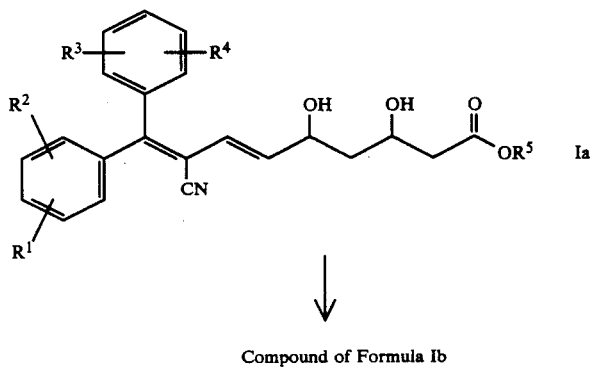
Compound of Formula Ib
Reaction Scheme 5
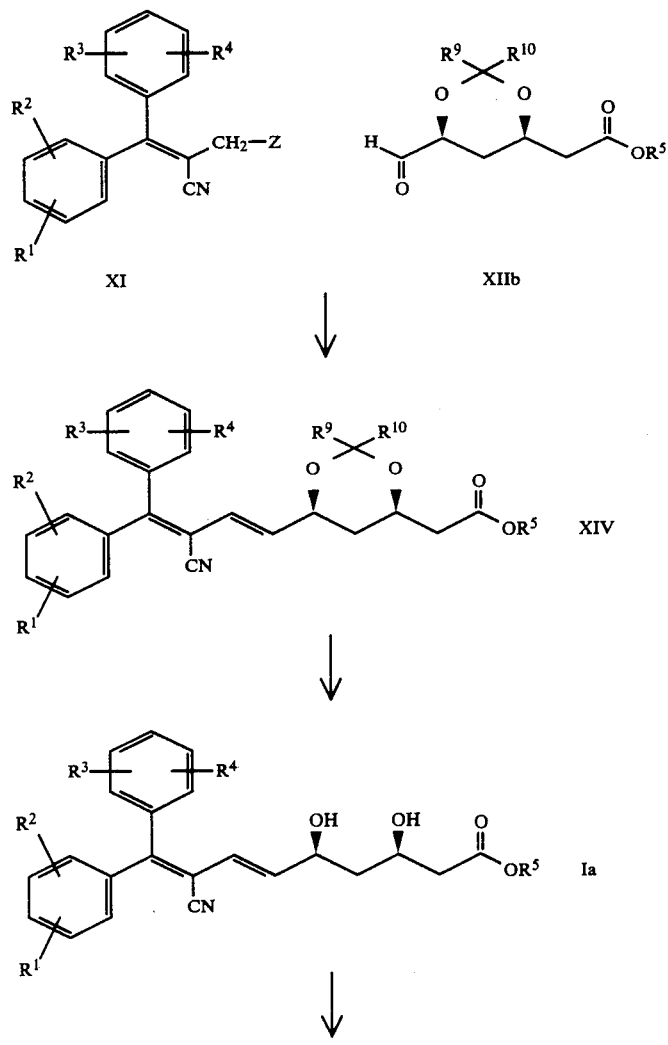
(4R, 6S) Compound of Formula Ib
In Reaction Schemes 4 and 5 $R^1$, $R^2$, $R^3$, $R^4$ and $R^5$, are as previously defined; Z is

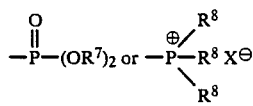

in which $R^7$ is $C_{1-4}$ alkyl, $R^8$ is phenyl which is unsubstituted or substituted by one or two $C_{1-4}$alkyl or chloro substituents; X is bromo, chloro or iodo and $R^9$ and $R^{10}$ each are independently hydrogen, $C_{1-6}$alkyl or phenyl which is optionally substituted by one or two $C_{1-4}$alkyl, halogen, $C_{1-4}$alkoxy or trifluoromethyl. The preparation of the phosphonium salt and the phosphonate of Formula XI is shown in Scheme 3. The reaction of a compound of Formula XI with a compound of Formula XIIa or Formula XIIb to produce a compound of Formula XIII or XIV respectively, wherein $R^5$ is $C_{1-4}$alkyl may be carried out in an inert organic solvent such as tetrahydrofuran and N,N-dimethylformamide in the presence of a strong base such as n-butyllithium at a temperature of about $-50°$ C. to about $-78°$ C. When the reaction of a compound of Formula XI is carried out with a compound of Formula XIIa or XIIb wherein $R^5$ is hydrogen, it is preferred to use two equivalents of a strong base such as n-butyllithium. Alternatively, the salt of a compound of Formula XIIa or XIIb may be prepared which is then treated with a compound of Formula XI and a strong base. The methods of addition, salt formation and ylide preparation are well-known to those skilled in the art. The nitrile compounds of Formula XIII or XIV may be readily deprotected by well-known procedures such as mild acid, e.g., 0.2N HCl and 0.5N HCl in an inert organic solvent such as tetrahydrofuran to produce the erythro compounds of Formula Ia or the (3R,5S) compounds of Formula Ia which may then be converted to the trans compounds of Formula Ib or (4R,6S) compounds of Formula Ib in a conventional manner well-known to those skilled in the art.

In a preferred embodiment of the invention the compounds of Formula I have the structure

I

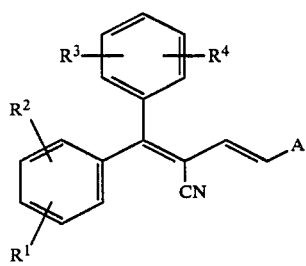

wherein
$R^1$, $R^2$, $R^3$ and $R^4$ each are independently hydrogen, fluoro, chloro, methyl or methoxy;
A is

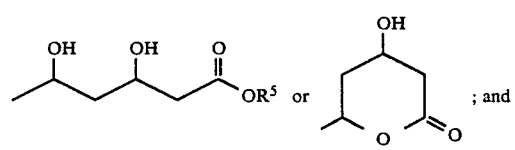

; and $R^5$ is hydrogen, a hydrolyzable ester group or a cation to form a non-toxic pharmaceutically acceptable salt.

In a more preferred embodiment of the invention the compounds of Formula I have the structure

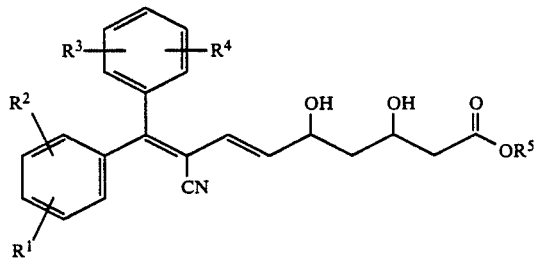

wherein $R^1$, $R^2$, $R^3$, and $R^4$ each are independently hydrogen, fluoro, chloro, or methyl; and $R^5$ is hydrogen, $C_{1-6}$ alkyl or a cation to form a non-toxic pharmaceutically acceptable salt.

In another more preferred embodiment of the invention the compounds of Formula I have the structure

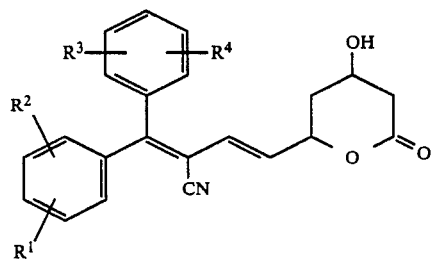

wherein $R^1$, $R^2$, $R^3$, and $R^4$ each are independently hydrogen, fluoro, chloro, or methyl.

In another aspect, this invention provides novel intermediates of the formula

XV

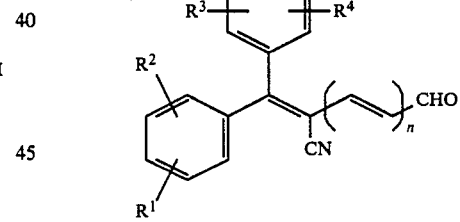

wherein $R^1$, $R^2$, $R^3$ and $R^4$ each are independently hydrogen, halogen, $C_{1-4}$ alkyl, $C_{1-4}$ alkoxy, or trifluoromethyl; and n is zero or 1.

In a preferred embodiment, the compounds of Formula XV have the structure

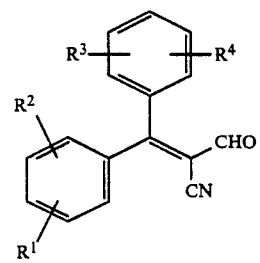

wherein $R^1$, $R^2$, $R^3$ and $R^4$ each are independently hydrogen, fluoro, chloro, or methyl.

In another preferred embodiment, the compounds of Formula XV have the structure

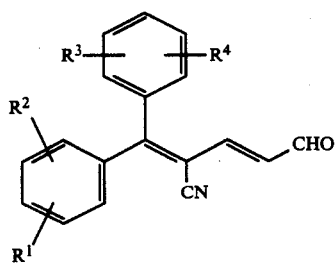

wherein $R^1$, $R^2$, $R^3$ and $R^4$ each are independently hydrogen, fluoro, chloro or methyl.

In still another aspect, this invention provides novel intermediates of the formula

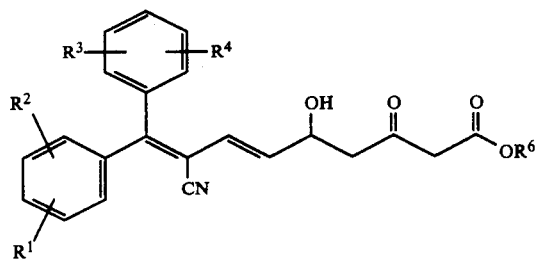

IX wherein $R^1$, $R^2$, $R^3$ and $R^4$ each are independently hydrogen, halogen, $C_{1-4}$alkyl, $C_{1-4}$alkoxy or trifluoromethyl; and $R^6$ is a hydrolyzable ester group.

The compounds of Formula I are competitive inhibitors of the enzyme 3-hydroxy-3-methylglutaryl coenzyme A (HMGCoA) reductase, the rate limiting enzyme in cholesterol biosynthesis, and therefore, are selective suppressors of cholesterol biosynthesis in animals, including man. Consequently, they are useful in the treatment of hypercholesterolemia, hyperlipoproteinemia and atherosclerosis The biological activity of the compounds of Formula I may be demonstrated in the following biological test.

In Vitro Inhibition of Microsomal HMG-CoA Reductase:

The intact, fully activated microsomal form of rat liver HMG-CoA reductase (subunit MW ca 100,000 daltons) was prepared as described by Parker, et al., *Biochem. Biophys Res. Commun.*, 125, 629–635 (1984), and used as the source of enzyme for assays. HMG-CoA reductase activity was determined essentially by the method of Shapiro, et al., *Biochem. Biophys. Acta.*, 370, 369–377 (1974). with modifications as described by Ingebritsen and Gibson *Meth. Enzymol.* 71, 486–497 (1981) with the exception that the internal standard $^3$H-mevalonolactone is added after termination of the assay. In this procedure the enzyme is assayed by measuring the formation of product, $^{14}$C-mevalonate, from the substrate, [3-$^{14}$C]-HMG-CoA, in the presence of NADPH. The $^{14}$C-mevalonate is converted to its lactone and isolated by silica thin-layer chromatography (Whatman LK5D, developed in 50:50 benzene:acetone) in the presence of $^3$H-mevalonolactone as an internal standard. Assays were conducted under conditions in which product formation was linear with respect to time and enzyme concentration.

To measure reductase inhibition, test compounds dissolved in water or dimethylsulfoxide and diluted in buffer A (50 mM imidazole-HCl, 250 mM NaCl, 1 mM EDTA, 1 mM EGTA, 5 mM DTT, 20 μM leupeptin, pH=7.2) were incubated with aliquots of microsomes (80–160 μg protein in buffer A) followed by addition of d,1-[3-$^{14}$C]-HMG-CoA (0.33 mM, 2.0 dpm/picomole) and NADPH (3.0 mM). The 50 percent inhibitory concentration $IC_{50}$) for each compound in Table 1 was calculated from the linear regression line of the percent decrease (from control) in enzyme activity vs. log concentration of inhibitor, determined using at least 4 dilutions of each test compound assayed in duplicate.

TABLE 1

| Inhibition of Microsomal HMG-CoA Reductase | |
|---|---|
| Compound of Example No. | $IC_{50}$ μmolar |
| 7 | 8.0 |
| 8 | 26.0 |

The results of the above Test demonstrates that the compounds of Formula I inhibit cholesterol biosynthesis and, therefore, are useful in the treatment of hypercholesterolemia.

In another embodiment, this invention includes pharmaceutical compositions comprising at least one compound of Formula I in combination with a pharmaceutical carrier or diluent.

In another embodiment, this invention relates to a method of inhibiting cholesterol biosynthesis in an animal in need thereof, which comprises administering to said animal an effective cholesterol inhibitory dose of at least one compound of Formula I.

For therapeutic use, the pharmacologically active compounds of Formula I will normally be administered as a pharmaceutical composition comprising as the (or an) essential active ingredient at least one such compound in association with a solid or liquid pharmaceutically acceptable carrier and, optionally, with pharmaceutically acceptable adjuvants and excipients employing standard and conventional techniques.

The pharmaceutical compositions may be administered orally, parenterally or by rectal suppository. A wide variety of pharmaceutical forms may be employed. Thus, if a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. If a liquid carrier is employed, the preparation may be in the form of a syrup, emulsion, soft gelatin capsule, sterile vehicle for injection, an aqueous or nonaqueous liquid suspension, or may be a dry product for reconstitution with water or other suitable vehicle before use. Liquid preparations may contain conventional additives such as suspending agents, emulsifying agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized. Injectable suspensions also may be used, in Which case conventional suspending agents may be employed. Conventional preservatives, buffering agents and the like also may be added to the parenteral dosage forms. The pharmaceutical compositions are prepared by conventional techniques appropriate to the desired preparation containing appropriate amounts of the active component, that is, the compound of Formula I according to the invention.

The compounds of Formula I may also be co-administered with pharmaceutically acceptable non-toxic cationic polymers capable of binding bile acids in a non-reabsorbable form in the gastrointestinal tract, e.g., cholestyramine, colestipol and poly [methyl-(3-trimethyl-aminopropyl)iminotrimethylene dihalide]. The relative amounts of polymer to compounds of this invention is between about 10:1 to about 10,000:1.

The dosage of the compounds of Formula I will depend not only on such factors as the weight of the patient and mode of administration, but also on the degree of cholesterol biosynthesis inhibition desired and the potency of the particular compound being utilized. The decision as to the particular dosage to be employed (and the number of times to be administered per day) is within the discretion of the physician, and may be varied by titration of the dosage to the particular circumstances of this invention for biosynthesis, each oral dosage unit will contain the active ingredient in an amount of from about 0.01 mg/kg to about 10 mg/kg body weight, and most preferably from about 0.05 mg/kg to about 2 mg/kg body weight. The active ingredient will preferably be administered in equal doses from one to four times a day. However, usually a small dosage is administered, and the dosage is gradually increased until the optimal dosage for the host under treatment is determined.

DESCRIPTION OF SPECIFIC EMBODIMENTS

In the following examples, all temperatures are given in degrees Centigrade. Melting points were recorded on a Haake-Buchler Melting Point Apparatus and are uncorrected. Proton magnetic resonance ($^1$H NMR) spectra were recorded on a Bruker AM 300, Burker WM 360, or Varian Gemini 300 Spectrometer. All spectra were determined in CDCl$_3$, DMSO-d$_6$ or D$_2$O unless otherwise indicated and chemical shifts are reported in $\delta$ units downfield from the internal standard tetramethylsilane (TMS) and interproton coupling constants are reported in Hertz (Hz). Splitting patterns are designated as follows s, singlet; d, doublet, t, triplet; q, quartet; m, multiplet; br, broad peak; dd, doublet of doublet; dt, doublet of triplet; and dq, doublet of quartet. Carbon-13 nuclear magnetic resonance ($^{13}$C NMR) spectra were recorded on a Bruker AM 300 or Varian VXL 200 spectrometer and were broad band proton decoupled. All spectra were determined in CDCl$_3$, DMSO-d$_6$ or D$_2$O unless otherwise indicated with internal deuterium lock and chemical shifts are reported in $\delta$ units downfield from tetramethylsilane. Infrared (IR) spectra were determined on a Nicolet MX-1 FT spectrometer from 4000 cm$^{-1}$ to 400 cm$^{-1}$, calibrated to 1601 cm$^{-1}$ absorption of a polystrene film and are reported in reciprocal centimeters (cm$^{-1}$). Relative intensities are indicated as follows: (strong), m (medium) and w (weak).

Mass spectra were recorded on a Kratos MS-25 instrument utilizing the fast atom bombardment (FAB) technique or on a Finnigan 4500 instrument utilizing the EI or CI technique. The mass data are expressed in the format parent ion (M+) or protonated ion (M+H)+.

Analytical thin-layer chromatography (TLC) was carried out on precoated silica gel plates (60F-254) and visualized using UV light, iodine vapors and/or staining with one of the following reagents: (a) methanolic phosphomolybdic acid (2%) and heating; (b) reagent (a) followed by 2% cobalt sulphate in 5M H$_2$SO$_4$ and heating. Column chromatography, also referred to as flash column chromatography, was performed in a glass column using finely divided silica gel (32–63 $\mu$m on silica gel-H) and pressures somewhat above atmospheric pressure with the indicated solvents. All evaporations of solvents were performed under reduced pressure. As used herein, the term hexanes is a mixture of isomeric C$_6$ hydrocarbons as specified by the American Chemical Society, and the term "inert" atmosphere is an argon or nitrogen atmosphere unless otherwise indicated.

EXAMPLE 1

Ethyl 2-cyano-3 3-bis(4-fluorophenyl)-2-propenoate

A mixture of 20.0 g (92 mmoles) of 4,4'-difluorobenzophenone, 11.0 g (97 mmoles) of ethyl cyanoacetate in a mixed solvent of 100 mL of dry benzene and 20 mL of glacial acetic acid containing a catalytic amount of $\beta$-alanine (0.9 g) was refluxed with separation of water using a Dean-Stark water trap. Separation of water was rapid during the first 2 hours (0.4 mL aqueous layer collected) but slower afterward. Azeotropic distillation was continued for a period of 14 days. Analytical TLC eluted with 10% EtOAc in hexanes (v/v) (Merck plate 0.25 mm Silica gel-F) showed two spots at R =0.2 (desired product) and at R$_f$=0.45 (4 4'-difluorobenzophenone starting material). Crude reaction mixture was washed with water (40 mL$\times$2), and the combined aqueous washes were extracted with EtOAc (150 mL$\times$2). The organic layers were combined, dried over MgSO$_4$ and concentrated under reduced pressure to crystallize the product as pale cubic crystals. The crude product was collected, washed with 1:1 EtOAc in hexanes (v/v) then recrystallized from 8:1 (hexanes:ethyl acetate v/v) to give 16.2 g (56.3%) of alytical pure title compound; m.p.=114°–116° C.

IR (KBr)$\nu_{max}$: 3000 (s), 2225 (s), 1931 (vs), 1605 (s), 1513 (s), 1250 (s), 844 (s) cm$^{-1}$.

$^1$H NMR (CDCl$_3$)$\delta$:1.19 (3H, t, J=7.1 Hz), 4.18 (2H, q, J=7.1 Hz), 7.08–7.15 (6H, m), 7.40–7.42 (2H, m).

$^{13}$C NMR (CDCl$_3$)$\delta$:13.75, 62.27, 104.05, 116.69, 115.53 (d, $^2$J$_{C-F}$=22.7 Hz), 115.88 (d, $^2$J$_{C-F}$=22.7 Hz), 131.64 (d, $^3$J$_{C-F}$=9.1 Hz), 134.25, 134,31, 134.36, 164.01 (d,$^1$J$_{C-F}$=252.9 Hz), 164,52 (d, $^1$J$_{C-F}$=254.0 Hz), 166.65 ppm.

Anal. Calcd. for C$_{18}$H$_{13}$NO$_2$F$_2$:
C, 69.01; H, 4.15; N, 4.47 .
Found: C, 68.91; H, 4.15; N, 4.62.

EXAMPLE 2

2-Cyano-3,3-bis(4-fluorophenyl)-2-propenoic acid

To a solution of ethyl 2-cyano-3,3-bis(4-fluorophenyl)-2-propenoate (5.0 g, 16 mmol) in tetrahydrofuran mL) at 0° C. was added a solution of 1 M lithium hydroxide in water (30 ML). Saponification reaction was allowed to proceed at 0° C. for a total of three hours forming a clear homogeneous solution. Crude reaction mixture was made acidic by adding 15 mL of 3 M HCl solution in water and the organic material was extracted twice into diethyl ether. Organic layers were combined, dried over MgSO$_4$ and concentrated under reduced pressure to give a pale solid. Recrystallization from ethyl acetate-hexanes mixture (1:9 v/v) yielded 3.08 g of the gigle compound; m.p.=180–181° C. Another 1.37 g of the desired product was also isolated from the mother liquor making the total combined yield of the title compound over 97%.

IR (KBr) $\nu_{max}$:3500 (br), 2210 (s), 1713 (s), 1625 (s), 1600 (s), 1225 (s), 1156 (s), 844 (s).

$^1$H NMR (DMSO-d$_6$)δ:7.47 (m, 2H), 7.35 (m, 2H), 7.28 (m, 4H), 7.2 (br, 4H).

$^{13}$C NMR (DMSO-d$_6$)δ:163.47, 163.10, 162.99, 134.73, 132.05, 131.94, 117.08, 115.07, 115.18, 105.56.

Anal. Calcd. for C$_{16}$H$_9$F$_2$O$_2$N:
C, 67.30; H, 3.20; N, 4.90.
Found: C, 65.98; H, 3.39; N, 4.81.

EXAMPLE 3

2-Cyano-3,3-bis(4-fluorophenyl)-2-propenal

A. 2-Cyano-3,3-bis(4 TM fluorophenyl)-2-propenoyl chloride

To a suspension of 2-cyano-3,3-bis(4-fluorophenyl)-2-propenoic acid (4 g, 14 mmol) in 10 mL of dry methylene chloride at room temperature was added oxalyl chloride (6 mL, 69 mmol) in one single portion. The reaction was stirred and warmed slowly to reflux for 45 minutes. The pale homogeneous solution was evaporated under reduced pressure to remove volatile solvent, then excess oxalyl chloride was removed under vacuum (20 mm Hg) at ambient temperature for 2 hours and under high vacuum (0.1 mm Hg) for 16 hours to give the title compound.

B. 2-Cyano-3,3-bis(4-fluorophenyl)-2-propenol

The acyl chloride prepared in Step A was dissolved in 40 mL of tetrahydrofuran and was chilled to −78° C. under an inert atmosphere. To this pale greenish solution at −78° C. was added 10 mL lithium aluminum hydride in tetrahydrofuran solution (1 M, 10 mmol). Reduction was allowed to proceed at −78° C. for 20 minutes before it was diluted with H$_2$SO$_4$ dilute solution (2 M, 20 mL). The desired product was extracted twice into ethyl acetate (40 mL×2). Organic layers were combined, dried over MgSO$_4$ and concentrated under reduced pressure to give 2.64 g (69.4%) of the title compound. The crude allylic alcohol was used in the next step without further purification. An analytically pure sample was prepared by crystallization from a mixture of ethyl acetate-hexanes (1:9, v/v) m.p.=110°–112° C.

IR (KBr) $\nu_{max}$:3500 (br), 2106 (s), 1750 (s), 1600 (s), 1510 (s).

$^1$H NMR (DMSO-d$_6$)δ:7.3–7.7 (m, 8H), 5.65 (t, 1H, J=5.4 Hz), 4.11 (d, 2H, J=5.4 Hz).

$^{13}$C NMR (DMSO-d$_6$)δ:164.5, 158.5, 154.5, 135.0, 131.5, 119.0, 115.4, 113.5, 59.6.

C. 2-Cyano-3,3-bis(4-fluorophenyl)-2-propenal

To a vigorously stirred solution of the crude allylic alcohol 0.51 g (1.9 mmol, prepared in Step B) in 14 mL of dry methylene chloride under an inert atmosphere at room temperature was added pyridinium chlorochromate (700 mg, 3.2 mmol) in one single portion. The oxidation was allowed to proceed at room temperature for 16 hours, during which all the starting material was consumed. The crude oxidation suspension was filtered through a bed of silica gel, washed with 25% (v/v) ethyl acetate in hexanes The desired product crystallized upon concentration under reduced pressure to give 0.5 g (quantitative yield) of the title compound; m.p. =167°–169° C. MS(CI): m/e=269 for M$^+$.

IR (KBr):$\nu_{max}$:2113 (s), 1713 (m), 1681 (s), 1600 (s), 1500 (s).

$^1$H NMR (CDCl$_3$)δ:9.38 (s, 1H), 7.55–7.51 (m, 2H), 7.33–7.15 (m, 6H).

$^{13}$C NMR (CDCl$_3$)δ:186.31, 170.29 165.26, 165.06, 133.5, 133.47, 133.17, 131.61, 116.48, 116.19, 115.27, 113.28.

Anal. Calcd. for C$_{16}$H$_9$F$_2$NO:C, 71.40; H, 3.30; N, 5.20.

Found: C, 71.09; H, 3.44; N, 5.16.

EXAMPLE 4

4-Cyano-5,5-bis(4-fluorophenyl)-2,4-pentadienal

To a dry mixture of 2-cyano-3,3-bis(4-fluorophenyl) TM 2-propenal (1.29 g, 4.8 mmol) and triphenylphosphoranylidene acetaldehyde (1.54 g, 5.04 mmol) under an inert atmosphere at ambient temperature was added 60 mL of dry benzene. The suspension was warmed to reflux temperature under an inert atmosphere and the reaction was allowed to proceed at reflux temperature for one hour. The crude reaction mixture was poured on a silica gel column saturated with hexanes. The desired product was eluted with 1 liter of hexanes followed by liter of 20% ethyl acetate in hexanes (v/V) to give 1.43 g (100%) of the title compound.

An analytically pure sample was obtained by recrystallization from a mixture of ethyl acetate in hexanes (8% v/v); m.p. 155°–156° C. MS(CI):m/e=296 for (M+H)$^+$.

IR (KBr) $\nu_{max}$:2110 (s), 1680 (s), 1595 (s), 1506 (s).

$^1$H NMR (CDCl$_3$)δ:9.57 (d, 1H, J=7.4 Hz), 7.48–7.44 (m, 2H), 7.24–7.10 (m, 7H), 6.73 (dd, 1H, J=7.4, 16 Hz).

$^{13}$C NMR (CDCl$_3$)δ:192.07, 164.38, 164.15, 144.82, 134.73, 134.69, 132 36, 132.47, 116.30, 115.84, 108.90.

Anal. Calcd. for C$_{18}$H$_{11}$F$_2$NO: C, 73.21; H, 3.75; N, 4.74

Found: C, 73.03; H, 3.85; N, 4.74.

EXAMPLE 5

Ethyl 8-cyano-9,9-bis(4-fluorophenyl)-5-hydroxy-3-oxo-6,8-nonadienoate

To a chilled suspension (0° C., ice-water bath) of sodium hydride (120 mg, 60% suspension in mineral oil, 3 mmol) in dry tetrahydrofuran (2 mL) under an inert atmosphere was added ethyl acetoacetate (330 μL, 2.6 mmol) in 4 equal portions over a period of 10 minutes. The homogeneous clear solution was stirred at 0° C. for 30 minutes followed by the dropwise addition of 2.5 M n-BuLi hexane solution (1.15 mL, 2.9 mmol) over 15 minutes. The orange dianion solution was stirred at 0° C. for an additional hour. The ice-water bath was replaced by an acetone-dry ice bath at −78° C. and the dianion solution was transferred via a cannula into a tetrahydrofuran (10 mL) solution containing 4-cyano-5,5-bis(4-fluorophenyl)-2,4-pentadienal (0.5 g, 1.7 mmol). The reaction mixture was allowed to stir at −78° C. for 5 minutes then was diluted with 40 mL of 1 M HCl aqueous solution. The organic material was extracted twice with ethyl acetate (50 mL×2). The organic layers were combined, dried over MgSO$_4$ and concentrated under reduced pressure. The desired product was partitioned over a silica gel column and eluted with 1.5 liters of 30% (v/v) ethyl acetate in hexanes to give 0.57 g (79%) of the title compound as a gummy solid.

¹H NMR (CDCl₃)δ:7.38–7.33 (2H, m), 7.18–7.04 (6H, m), 6.50 (1H, d, J=15.6 Hz), 6.41 (1H, dd, J=5.04, 15.6 Hz), 4.73 (1H, br), 4.19 (2H, q, J=7.1 Hz), 3.47 (2H, s), 3.22 (1H, br), 2.83–2.81 (2H, m), 1.28 (3H, t, J=7.1 Hz).

¹³C NMR (CDCl₃)δ:202.32, 166.79, 163.49, 163.23, 153.93, 136.92, 134.36, 134.08, 132.44, 132.24, 132.14, 124.79, 117.49, 115.81, 115.60, 110.31, 67.31, 61.57, 49.85, 49.14, 14.07.

EXAMPLE 6

Ethyl (±)-erythro-8-cyano-9,9-bis(4-fluorophenyl)-3,5-dihydroxy-6,8-nonadienoate To a solution of ethyl 8-cyano-9,9-bis(4-fluorophenyl)-5-hydroxy-3-oxo-6,8-nonadienoate (0.49 g, 1.15 mmol) in 8 mL of dry tetrahydrofuran at 0° C. (ice-water bath) under an inert atmosphere was added triethylborane solution in tetra ™ hydrofuran (1 M, 1.4 mL, 1.4 mmol) in one single portion. The pale mixture was stirred for a total of one hour. The cooling ice-water bath was replaced with an acetone-dry ice bath and to the reaction mixture was added NaBH₄ (56 mg, 1.48 mmol) in one portion. The reaction suspension was stirred at −78° C. for two hours forming a clear homogeneous pale yellow solution. The crude mixture was diluted with 200 μL of reagent grade methanol and the solution was allowed to stir at −78° C. for an additional 1.5 hours. The crude reaction mixture was diluted with 30 mL of 1 M HCl aqueous solution followed by extractions with ethyl acetate (40 mL×2). The organic layers were combined, dried over MgSO₄ and concentrated under reduced pressure to give the product as a thick syrup, it was further diluted with 50 mL of dry methanol and the methanolic solution was allowed to stand at room temperature for 16 hours before evaporation under reduced pressure. The crude product was purified by flash silica gel column chromatography using 2 liters of 40% ethyl acetate in hexanes (v/v) as the eluting solvent. The appropriate fractions were collected and evaporated to give 0.40 g (72%) of the title compound. MS(CI) m/e=392 for (M-2H₂O)H⁺.

IR (KBr)ν$_{max}$:3450 (s), 2110 (s), 1729 (s), 1600 (s), 1506 (s), 1230 (s).

¹H NMR (CDCl₃)δ:7.37–7.32 (2H, m), 7.16–7.04 (6H, m), 6.55 (1H, d, J=15 Hz), 6.37 (1H, dd, J=15, 5 Hz), 4.58 (1H, m), 4.32 (1H, m), 4.17 (2H, q, J=7 Hz), 3.83 (2H, d, J=6Hz), 2.49 (2H, d, J=6 Hz), 1.69 (2H, m), 1.28 (3H, t, J=7 Hz).

¹³C NMR (CDCl₃)δ:172.48, 163.34, 163.05, 153.53, 138.54, 135.73, 134.18, 132.3, 132.0, 123.87, 115.7, 115 4, 117.59, 110.62, 71.44, 68.50, 60.93, 42.34, 41.49, 14.15.

Anal. Calcd. for C₂₄H₂₃F₂NO₄: C, 67.44; H, 5.42; H, 3.28.

Found: C, 63.02; H, 5.36; H, 3.00.

EXAMPLE 7

Sodium (±)-(E)-erythro-8-cyano-9,9-bis(4-fluorophenyl)-3,5-dihydroxy-6,8-nonadienoate To a solution of ethyl (±)-(E)-erythro-8-cyano-9,9-bis(4-fluorophenyl)-3,5-dihydroxy-6,8-nonadienoate (36 mg, 0.086 mmol) in 1.0 mL of reagent grade tetrahydrofuran at 0° C. (ice-water bath) under an inert atmosphere was added 1.0 M sodium hydroxide solution in water (84 μL, 0.084 mmol) dropwise over a period of five minutes. The rate of addition was adjusted so that no change of color of the reaction mixture developed. The saponification reaction was allowed to stir at 0° C. for a total of 3.5 hours and the crude mixture was lyophilized to give the title compound in quantitative yield.

IR (KBr)ν$_{max}$:3438 (s), 2113 (m), 1600 (s), 1579 (s), 1506 (s), 1234 (s).

¹H NMR (DMSO-d₆)δ:7.5–7.4 (2H, m), 7.4–7.2 (6H, m), 7.19 (1H, br), 6.4–6.2 (2H, m), 5.24 (1H, br), 4.31 (1H, m), 3.74 (1H, m), 3.08 (1H, dd, J=15, 1 Hz), 1.89 (1H, dd, J=15, 7 Hz), 1.62–1.40 (2H, m).

¹³C NMR (DMSO-d₆)δ:176.04, 162.48, 162.29, 152.20, 140.75, 135.90, 133.98, 132.08, 131.77, 122.04, 117.21, 115.64, 115.35, 110.64, 67.69, 65.61, 44.24, 43.54.

Anal Calcd. for C₂₂H₁₈F₂NO₄Na:
C, 62.71; H, 4.31; N, 3.32.
Found: C, 61.86; H, 4.77; N, 3.14.

EXAMPLE 8

Trans-(E)-2-[bis(4-fluorophenyl)methylene]-4-(tetrahydro-4-hydroxy-6-oxo-2H-pyran-2-yl)-3-butenenitrile

A.

(±)-Erythro-8-cyano-9,9-bis(4-fluorophenyl)-3,5-dihydroxy-6,8-nonadienoic acid

To a solution of ethyl (±)-erythro-8-cyano-9,9-bis(4-fluorophenyl)-3,5-dihydroxy-6,8-nonadienoate (109.3 mg, 0.26 mmol) in 2 mL of reagent grade tetrahydrofuran at 0° C. (ice-water bath) was treated with 259 μL of 1.0 M sodium hydroxide solution. The pale yellow suspension was stirred at 0° C.(ice-water bath) for two hours forming a clear pale yellow solution. The crude reaction mixture was diluted with 0.5 mL of aqueous HCl (1.0 M) solution and the organic product was extracted into ethyl acetate (30 mL×2). The organic extracts were combined, dried over MgSO₄ and concentrated under reduced pressure to give a pale gum. The crude free acid (117 mg) was rigorously dried under high vacuum (0.01 mm Hg) at room temperature for 24 hours before reacting in the next step.

B.

Trans-(E)-2-[bis(4-fluorophenyl)methylene]-4-(tetrahydro-4-hydroxy-6-oxo-2H-pyran-2-yl)-3-butenenitrile The dried acid from Step A was dissolved in 4.0 mL of dry methylene chloride at room temperature. To this stirring solution was added 0.3 g (0.71 mmol) of 1-cyclohexyl-3-(2-morpholinoethyl)carbodiimide metho-p-toluene sulfonate. Lactonization was complete in 12 hours at ambient temperature. Most of the solvent was evaporated under reduced pressure and the residue was washed with water (30 mL) followed by extractions with ethyl acetate (30 mL×2). The organic layers were combined, dried over MgSO₄ and concentrated under reduced pressure to give a pale yellow syrup. The crude product was filtered through a short bed of silica gel and eluted with 40% ethyl acetate in hexanes (v/v) to give 97 mg (98%) of the title compound. MS(CI) m/e=382 for (M+H)⁺.

IR (KBr)ν$_{max}$:3450 (s), 2113 (s), 1735 (s), 1600 (s), 1506 (s), 1233 (s), 750 (s).

¹H NMR (CDCl₃)δ:7.37–7.32 (2H, m), 7.16–7.02 (6H, m), 6.48 (1H, d, J=15.6 Hz), 6.33 (1H, dd, J=15.6, 5.9 Hz), 5.27 (1H, m), 4.40 (1H, br), 2.76 (1H, dd, J=4.6, 17.6 Hz), 2.62 (1H, dd, J=2.1, 17.6 Hz), 2.16 (1H, br), 2.05 (1H, d, J =14 Hz), 1.87 (1H, dt, J=2.6, 10.9 Hz).

$^{13}C$ NMR (CDCl$_3$)δ:169.11, 164.2, 164.0, 155.39, 136.1, 134.2, 133.12, 132.32, 132.02, 126.66, 117 27, 115.94, 115.67, 109.72, 74.92, 62.57, 38.68, 36.07.

Anal. Calcd. for $C_{22}H_{17}F_2NO_3$:

C, 63.31; H, 5.07; N, 3.36.

Found: C, 63.90: H, 5.17; N, 3.15.

What is claimed is:

1. A compound of the formula

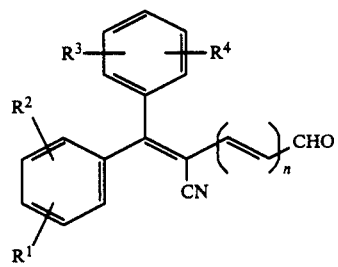

wherein
$R^1$, $R^2$, $R^3$ and $R^4$ each are independently hydrogen, halogen, $C_{1-4}$alkyl, $C_{1-4}$alkoxy, or trifluoromethyl; and
n is zero or 1.
2. A compound of claim 1 wherein n is zero.
3. A compound of claim 1 wherein n is 1.
4. A compound of claim 2 wherein $R^1$, $R^2$, $R^3$ and $R^4$ each are selected from the group consisting of hydrogen, fluoro, chloro and methyl.
5. A compound of claim 3 wherein $R^1$, $R^2$, $R^3$, and $R^4$ each are selected from the group consisting of hydrogen, fluoro, chloro and methyl.

* * * * *